United States Patent [19]

Mehta

[11] 4,365,072

[45] Dec. 21, 1982

[54] BIPHENYL ALDEHYDES

[75] Inventor: Avinash C. Mehta, Belmont, Mass.

[73] Assignee: Polaroid Corporation, Cambridge, Mass.

[21] Appl. No.: 313,942

[22] Filed: Oct. 22, 1981

[51] Int. Cl.³ .................. C07D 304/06; C07D 307/12; C07C 69/773
[52] U.S. Cl. .................... 549/415; 549/473; 560/108; 560/144; 568/441; 260/463
[58] Field of Search ................ 568/441; 560/144, 108; 260/345.9 R, 347.8, 463; 549/415, 473

[56] References Cited

U.S. PATENT DOCUMENTS

| | | | |
|---|---|---|---|
| 2,651,644 | 9/1953 | Gisrold | 568/441 |
| 3,406,064 | 10/1968 | Land . | |
| 3,600,177 | 8/1971 | Abbott et al. | |
| 3,617,272 | 11/1971 | Stewart . | |
| 3,617,277 | 11/1971 | Stewart . | |
| 4,085,147 | 4/1978 | Rosinger et al. | |
| 4,275,241 | 6/1981 | Bohm et al. | |
| 4,279,987 | 7/1981 | Ogi et al. | |

*Primary Examiner*—Johnnie R. Brown
*Assistant Examiner*—Frederick W. Pepper
*Attorney, Agent, or Firm*—Louis G. Xiarhos

[57] ABSTRACT

Biphenyl compounds of the formula

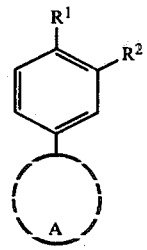

wherein one of $R^1$ and $R^2$ is hydrogen and the other is —CHO and the cyclic moiety A is a -2,5-; 2,3; or 3,4-di-OR-1-phenyl moiety wherein R is hydrogen or a hydroxy-protecting group are disclosed. The compounds are useful as intermediates in preparing redox compounds containing a phenylhydroquinone or phenylcatechol moiety.

13 Claims, No Drawings

BIPHENYL ALDEHYDES

BACKGROUND OF THE INVENTION

The present invention relates to novel intermediate compounds which are useful in preparing redox reagents comprising a phenylhydroquinone or phenylcatechol moiety.

Compounds having phenylhydroquinone or phenylcatechol moieties are of interest for employment as redox reagents, i.e., as reducing or electron-transfer agents in redox reactions. For example, such compounds are of interest in the photographic art for employment as redox reagents in photographic products and processes, e.g., as silver halide developing agents or auxiliary developing agents. The compound 4-phenylcatechol, for example, is disclosed in U.S. Pat. Nos. 3,617,272 and 3,617,277 to be useful as an auxiliary developing agent and as a chelating agent in certain diffusion transfer photographic elements. 4'-Methylphenylhydroquinone is a particularly useful compound which has been employed in various applications in diffusion transfer photograhic processes. U.S. Pat. No. 3,406,064 discloses the use of 4'-methylphenylhydroquinone as a silver halide developing agent in diffusion transfer processes for forming silver images. The employment of 4'-methylphenylhydroquinone as an auxiliary developing agent in color diffusion transfer processes is well known and is described by E. H. Land in Photographic Journal, 114, 338 (1974).

With regard to the photographic utility of compounds containing phenylhydroquinone or phenylcatechol moieties, it is believed that the biphenyl ring structure of these moieties contributes redox properties to the compounds rendering them particularly suitable for employment in various photographic applications. Accordingly, there has been a desire in the photographic art to provide compounds containing a phenylhydroquinone or phenylcatechol moiety such that the redox characteristics normally exhibited by these moieties may be used to advantage.

SUMMARY OF THE INVENTION

The present invention relates to novel compounds which are useful as intermediates that can be reacted to prepare a wide variety of product compounds containing a phenylhydroquinone or phenylcatechol moiety. The compounds of this invention are biphenyl aldehydes of the formula

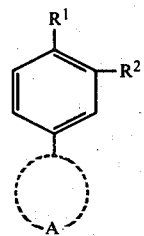

(I)

wherein one of $R^1$ and $R^2$ is hydrogen and the other is —CHO and the cyclic moiety A is a -2,5-; -2,3-; or -3,4-di-OR-1-phenyl moiety wherein R is hydrogen or a hydroxy-protecting group. The formyl group, —CHO, of the compounds of this invention can, in general, undergo the numerous reactions of aromatic aldehyde functions to provide product derivatives. When R is hydrogen, reaction of the formyl group can provide the desired phenylhydroquinone or phenylcatechol containing compound directly whereas, if R is a hydroxy-protecting group, reaction of the formyl group provides an intermediate product derivative which can be deblocked to remove the protecting group and provide the desired phenylhydroquinone or phenylcatechol containing compound. Compounds containing the phenylhydroquinone or phenylcatechol moiety can be employed as redox reagents, e.g., as antioxidants or as developing agents in photographic processes.

In a preferred embodiment the compounds of this invention are of the formula

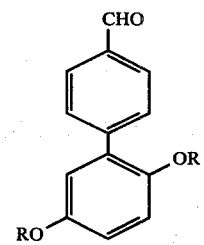

wherein R is as previously defined.

DETAILED DESCRIPTION OF THE INVENTION

As indicated previously, the present invention relates to compounds which can be employed as intermediates in the preparation of compounds containing a phenylhydroquinone moiety, and specifically a moiety of the formula

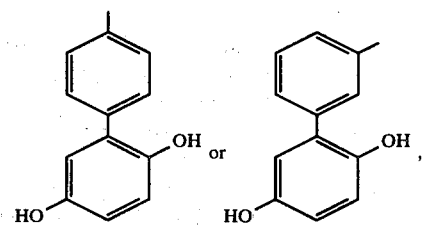

or a phenylcatechol moiety, specifically a moiety of the formula

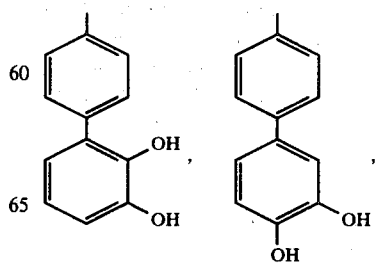

-continued

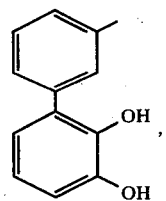, or 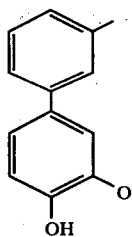

In the above formulas, the unattached valence bond shows the point of attachment of the moiety to the remainder of the redox compound.

The compounds of this invention are of the formula

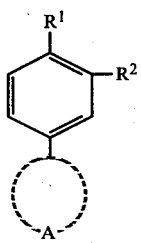 (I)

wherein one of $R^1$ and $R^2$ is hydrogen and the other is —CHO and the cyclic moiety A is a -2,5-; -2,3-; or -3,4-di-OR-1-phenyl moiety, i.e., a moiety of the formula

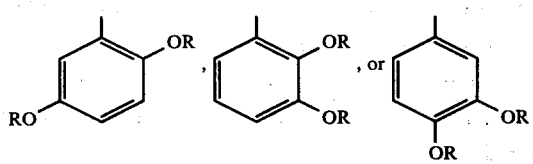

wherein R is hydrogen or a hydroxy-protecting group. In accordance with formula (I), the compounds of this invention can be referred to as 3'- or 4'-formyl-x,y-di-OR-1,1'-biphenyls wherein -x,y- is -2,5; -2,3; or -3,4-.

The cyclic moiety A may be substituted with substituents in addition to the —OR groups. Such substituents should be stable to and compatible with the reagents and reaction conditions employed in subsequent reactions of the instant compounds. Such substituents and the substitution pattern thereof on a compound of this invention will generally affect the oxidation-reduction potential of a redox material ultimately prepared from the compound. Generally, electron-attracting substituents will increase the redox potential of the material and electron-donating groups will lower it. Substituents in addition to —OR which may be present in the cyclic moiety A include lower alkoxy, nitro, cyano, carboxy, sulfo, formyl, chloro, bromo, and iodo, as well as carboxamido groups, e.g.,

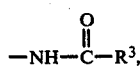

and acyl groups, e.g., $$-\overset{O}{\underset{\|}{C}}-R^4$$

wherein $R^3$ and $R^4$ are alkyl.

In the compounds of this invention wherein R is hydrogen, the formyl group can be reacted to provide the desired redox compound directly whereas if R is a hydroxy-protecting group it is necessary to both react the formyl group and deblock the hydroxy groups to provide the desired redox compound. Thus, when R is hydrogen, the desired redox compound may be provided by a single reaction involving appropriate derivatization of the formyl group. When R is a hydroxy-protecting group, reaction of the formyl group will, in general, provide a blocked or protected product derivative which is then deblocked to provide the desired redox compound.

It should be understood that provision of the desired redox compound may require a multi-step synthesis in which reaction of the formyl group is the first step and the resultant derivative is further reacted to provide the desired product. Where R is a hydroxy-protecting group, the deblocking reaction may be conducted at any suitable point in the synthetic sequence.

For certain reactions, the use of compounds of this invention wherein R is a hydroxy-protecting group will be preferred. The hydroxy-protecting group may provide any of a number of functions such as preventing oxidation of the hydroquinone or catechol moiety, providing favorable inductive effects so as to increase the reactivity of the formyl group or decrease the reactivity of unsubstituted sites on the di-OR-phenyl ring, or allowing more facile isolation of a reaction product, e.g., by imparting desired solubility characteristics to the product. The hydroxy-protecting groups may provide such functionality during preparation of the instant compounds or in conjunction with reaction of the formyl group or of derivatives formed by such reaction.

Various hydroxy-protecting groups are well known in the art and may be used in the compounds of this invention. Suitable groups are those capable of removal under acidic, neutral, or basic conditions so as to regenerate the hydroxy groups. Inasmuch as the hydroxy-protecting groups are intended to be removed from a derivative of a compound of this invention, they should be capable of removal under conditions appropriate for the derivative. Thus, if a particular derivative is insoluble or unstable in acidic media, hydroxy-protecting groups capable of removal under neutral or basic conditions will generally be preferred. Additional considerations regarding the choice of a particular hydroxy-protecting group can include the ease with which a compound of this invention can be prepared to comprise a given protecting group, the degree of difficulty associated with removal of the protecting group, and the ability of the protecting group to perform any of the above-noted functions. Among the various hydroxy-protecting groups which may be used in the compounds of this invention, specific mention may be made of lower alkyl having 1 to 6 carbon atoms such as methyl, ethyl, isopropyl, and tert-butyl; methoxymethyl; methylthiomethyl; phenacyl; p-bromophenacyl; 2-tetrahydrofuranyl; 2-tetrahydropyranyl; ethoxycarbonyl; 2,2,2-trichloroethoxycarbonyl; and acyl, e.g., acetyl and benzoyl.

Specific examples of the compounds of this invention are those having the following structures:
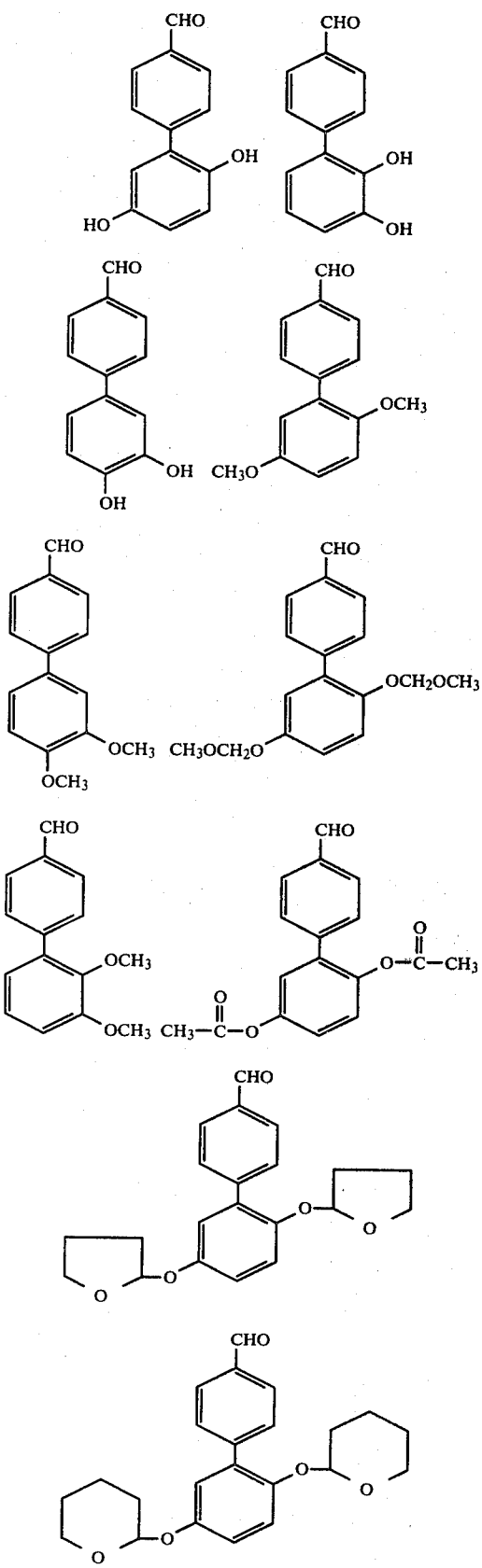
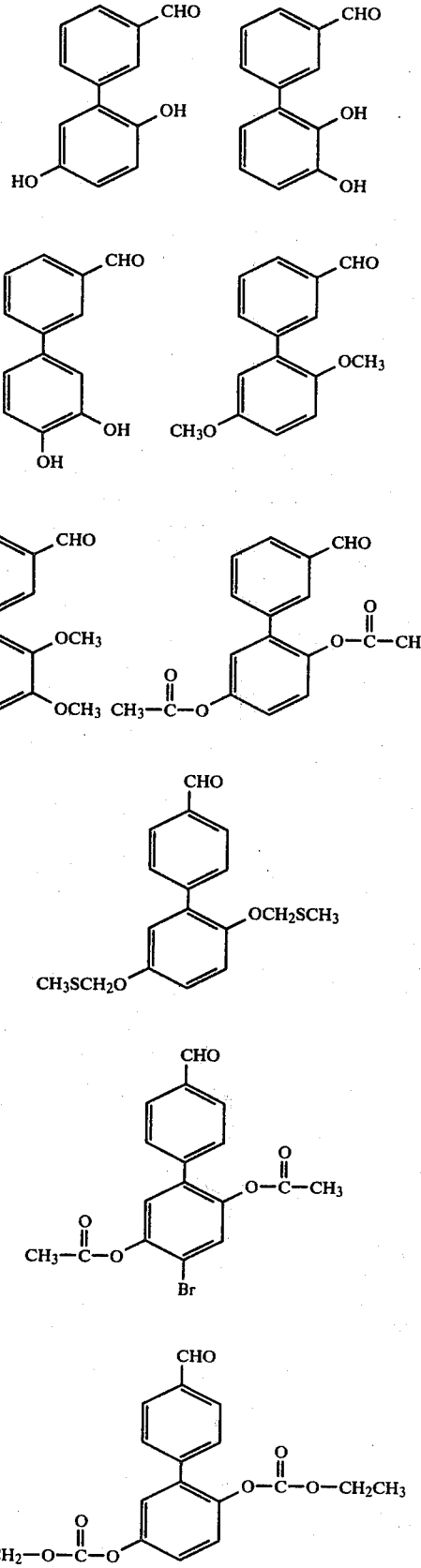

-continued

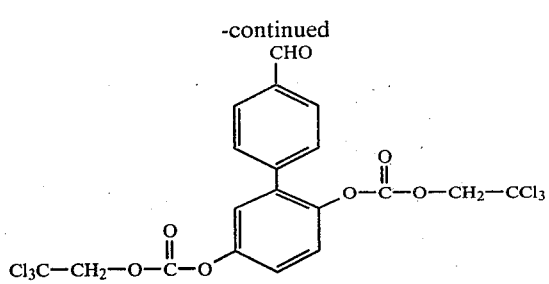

Preferred compounds of this invention are those of the formula

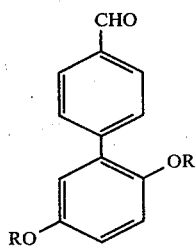

wherein R is as previously defined. These preferred compounds provide the capability of preparing compounds comprising a 4'-methylenephenylhydroquinone moiety and thus allow provision of various compounds comprising a moiety analogous to 4'-methylphenylhydroquinone. As previously indicated, 4'-methylphenylhydroquinone has proven to be a particularly useful redox reagent in diffusion transfer photographic processes.

The compounds of this invention can be prepared by converting the halomethyl group of a 3'- or 4'-halomethyl-x, y-di-OR$^5$-1,1'-biphenyl, wherein R$^5$ is a hydroxy-protecting group and the halo moiety is chloro or bromo, to a formyl group. This method of preparation is illustrated below using a 4'-bromomethyl-2,5-di-OR$^5$-1,1'-biphenyl as a representative starting material:

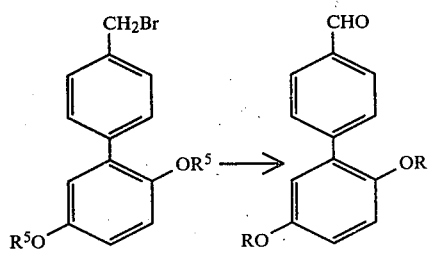   (1)

The reaction may be conducted using well known reactants and procedures for effecting conversion of alkyl halide groups to a formyl group. Thus, the halomethyl compound can be converted to the desired formyl compound by reaction with an aromatic N-oxide such as pyridine N-oxide, α-picolinium N-oxide, or quinoline N-oxide followed by treatment of the thus-formed product with base as described, for example, by W. Feely et al., J. Org. Chem., 22, 1135 (1957) or V. J. Traynelis et al., J. Org. Chem., 40:16, 2365 (1975); by reaction with dimethylsulfoxide followed by treatment of the thus-formed product with base as described, for example, by N. Kornblum et al., J. Am. Chem. Soc., 81, 4113 (1959); or by reaction with hexamethylene tetramine as described, for example, by S. J. Angyal et al., J. Chem. Soc., 2700 (1949) or S. J. Angyal, Org. React., 8, 197 (1954).

The hydroxy-protecting group R$^5$ can be any of the groups also suitable for use as the hydroxy-protecting group R. With reference to reaction (1), those R$^5$ groups stable to the conditions of the reaction will be maintained intact during the reaction and R in the final product and R$^5$ will be the same. However, certain of the hydroxy-protecting groups which can be used in the compounds of this invention, and as R$^5$, such as acyl, ethoxycarbonyl, and 2,2,2-trichloroethoxycarbonyl, can undergo hydrolysis in the presence of aqueous base or aqueous acid. Thus, the use of aqueous acid or base in the above-mentioned reactions may result in hydrolysis of such R$^5$ protecting groups. The resultant product is a compound of this invention wherein R is hydrogen. If it is desired to minimize or prevent hydrolysis during the above-mentioned base treatment steps, an appropriate base may be used under anhydrous conditions, e.g., sodium bicarbonate, sodium hydride, or triethylamine in an anhydrous solvent such as acetonitrile. If the hydroxy-protecting groups are hydrolyzed, but protecting groups are desired in the final product, the resultant dihydroxy compound can be reacted according to conventional procedures to "reblock" the hydroxy groups.

Illustrative preparations are shown in the following reaction schemes employing 4'-bromomethyl-2,5-diacetoxy-1,1'-biphenyl and 4'-bromomethyl-2,5-dimethoxy-1,1'-biphenyl as starting materials and α-picolinium N-oxide and aqueous hydroxide anion as reagents. In reaction scheme (1a), the acetyl protecting groups are illustrated as being hydrolyzed by the aqueous hydroxide and reintroduced by the known procedure of blocking the hydroxy groups with acetic anhydride in the presence of triethylamine. The following reaction schemes are illustrative only and not intended to be of limiting effect:

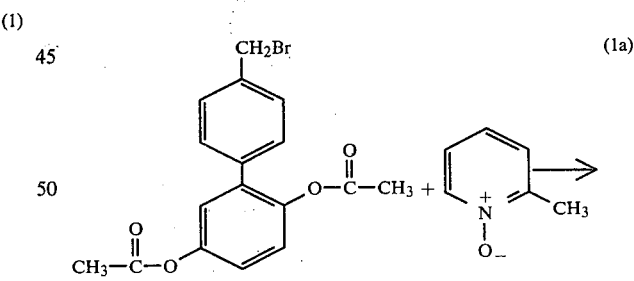   (1a)

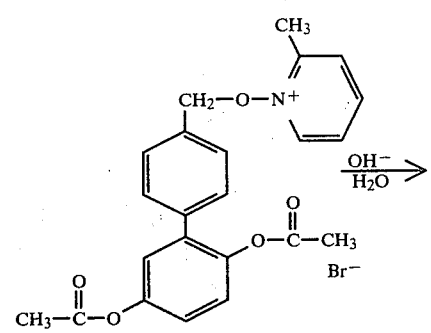

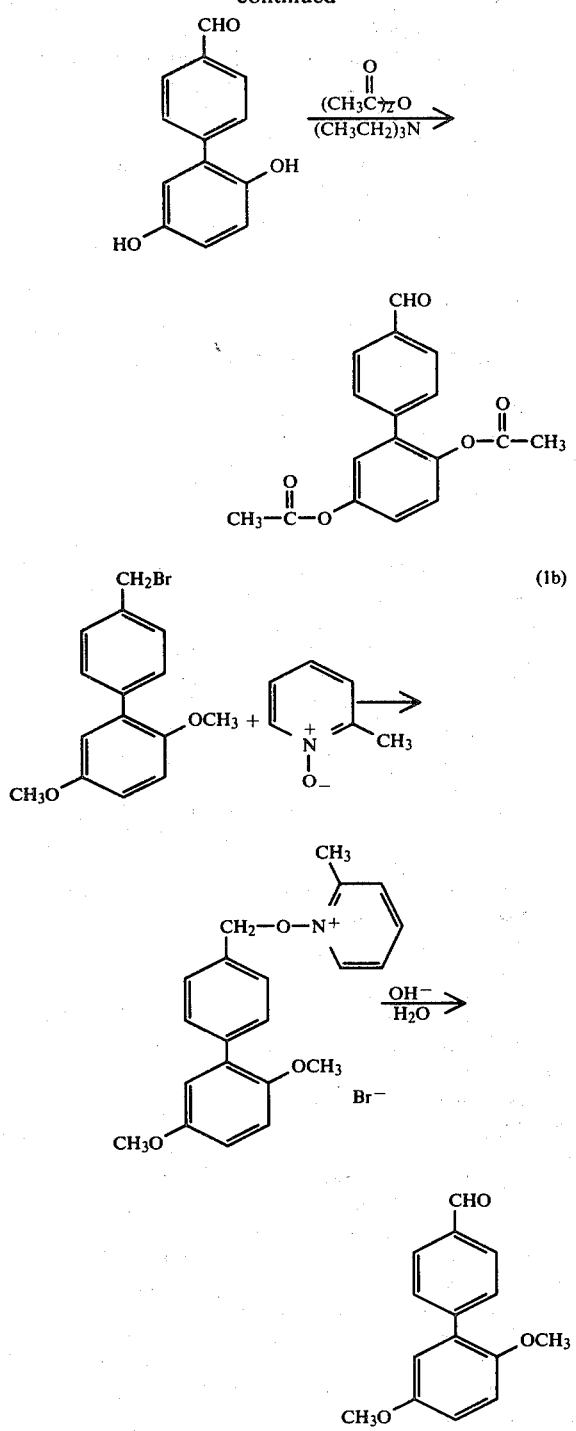

In a preferred method of preparation, the compounds of this invention are prepared by hydrolysis of the dihalomethyl group of a 3'- or 4'-dihalomethyl-x,y-di-$OR^5$-1,1'-biphenyl, wherein the halo moiety is chloro or bromo and $R^5$ is as previously defined. This method of preparation is illustrated below using a 4'-dibromomethyl-2,5-di-$OR^5$-1,1'-biphenyl as a representative starting material:

Various methods for hydrolyzing benzal halides to the corresponding aldehydes are known and any suitable method may be used to prepare the compounds of this invention. Thus, the dihalomethyl compound may be hydrolyzed to the desired formyl compound by reaction with sodium carbonate as described, for example, by J. J. Brown et al., Can. J. Chem., 33, 1819 (1955); by reaction with aqueous silver nitrate in methyl cellosolve as described, for example, by H. Gilman et al., J. Am. Chem. Soc., 78, 1689 (1956); by reaction with sodium formate in aqueous alcohol as described, for example, by E. Eliel et al., J. Chem. Soc., 1628 (1955); or by reaction with sodium acetate in acetic acid as described, for example, by W. Reid et al., Chem. Ber., 91, 2479 (1958). In a preferred method, the hydrolysis is carried out by reacting the dihalomethyl starting material with an alkali metal acetate, such as sodium acetate, in an aqueous alcohol solution, preferably aqueous methanol, and treating the resultant product mixture with hydrochloric acid. The starting material is believed to react with both the acetate and alcohol to effect displacement of both halide moieties and production of a mixture of products which are then hydrolyzed directly to the desired aldehyde compound by the hydrochloric acid. As indicated by Example 4 herein, this preferred method provides the compounds of this invention in high yield and good purity.

As with the preparative method illustrated above by reaction (1), the hydroxy-protecting group $R^5$ in the starting material for reaction (2) can be any of the groups also suitable for use as the hydroxy-protecting group R and certain $R^5$ groups may undergo displacement during the reaction. With regard to the preferred method of conducting the hydrolysis, wherein aqueous hydrochloric acid is employed, those $R^5$ groups possessing sufficient stability in the presence of this acid will be maintained intact during the reaction and R in the final product and $R^5$ will be the same. However, certain of the hydroxy-protecting groups which can be used as $R^5$, such as acyl, ethoxycarbonyl, and 2,2,2-trichloroethoxycarbonyl, may undergo at least partial hydrolysis in the presence of the aqueous hydrochloric acid with resultant formation of a compound of this invention wherein R is hydrogen. As indicated above in regard to reaction (1), such a compound can be "reblocked" by conventional procedures of blocking phenolic hydroxy groups.

Illustrative preparations are shown in the following reaction schemes employing 4'-dibromomethyl-2,5-diacetoxy-1,1'-biphenyl and 4'-dibromomethyl-2,5-dimethoxy-1,1'-diphenyl as starting materials and sodium acetate, methanol, and hydrochloric acid as reagents. In reaction scheme (2a), the acetyl groups are illustrated as being hydrolyzed by the hydrochloric acid and then reintroduced in the previously described manner. The following reaction schemes are illustrative only and not intended to be of limiting effect:

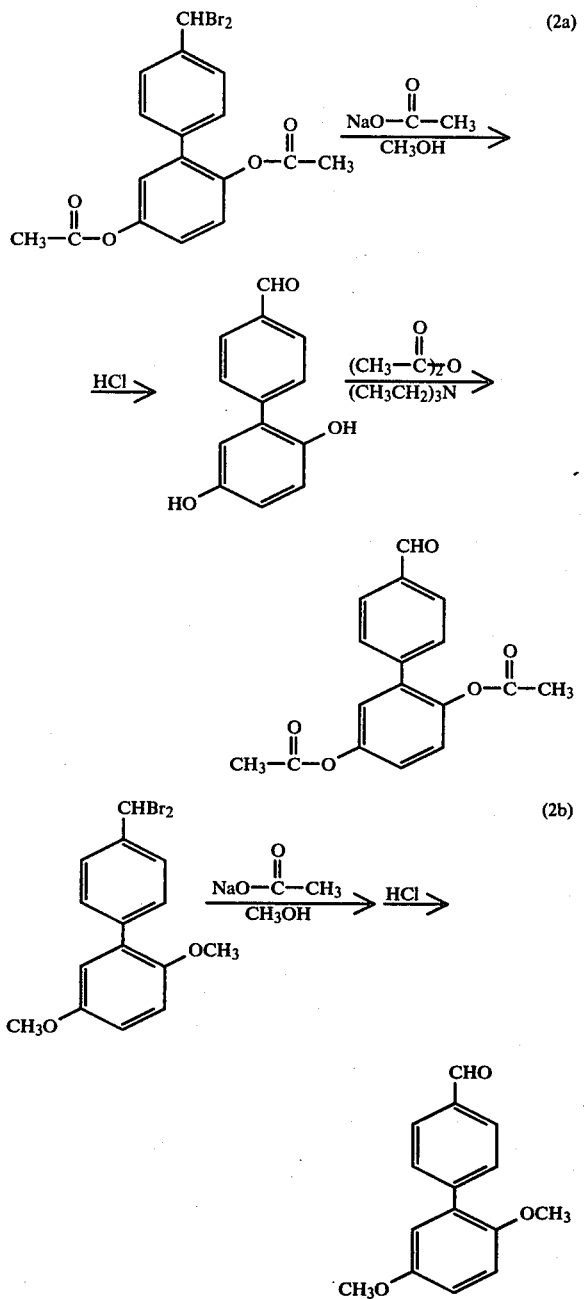

With regard to reblocking the hydroxy groups of the compounds of this invention it should be noted that various methods of blocking hydroxy groups with removable protecting groups are well known. Any of the known methods may be employed provided that there is not an unacceptable accompanying side reaction of the formyl group. Methods which may be employed include methylation with dimethylsulfate; acylation with acetic anhydride in the presence of a basic catalyst; methoxymethylation as described, for example, by Kaoru Fuji et at., Synthesis, 4, pp. 276–277 (1975); tetrahydrofuranylation as described, for example, by C. G. Kruse et al., Tetrahedron Lett., 20, p. 1725 (1976); tetrahydropyranylation as described, for example, by W. F. Parham et al., J. Am. Chem. Soc., 70, pp. 4187–4189 (1948); and trichloroethoxycarbonylation as described, for example, by Just et al., Synthesis, p. 457, (1976).

The 3'- or 4'-halomethyl and dihalomethyl-x,y-di-OR$^5$-1,1'-diphenyls used as starting materials in the above preparative methods constitute the subject matter of the copending U.S. patent application Ser. No. 313,944, of A. C. Mehta, filed of even date. In accordance with the disclosure therein, the halomethyl and dihalomethyl compounds can be prepared by blocking the hydroxy groups of a 3'- or 4'-methyl-x,y-dihydroxy-1,1'-biphenyl with hydroxy-protecting groups to form the corresponding 3'- or 4'-methyl-x,y-di-OR$^5$-1,1'-biphenyl wherein R$^5$ is the hydroxy-protecting group and reacting that product with a benzylic chlorinating or brominating agent to form the corresponding 3'- or 4'-halomethyl or dihalomethyl-x,y-di-OR$^5$-1,1'-biphenyl. With regard to this method of preparation, the relative molar amount of benzylic chlorinating or brominating agent will generally determine whether the halomethyl or dihalomethyl species is provided.

In general, those procedures commonly used in the art for removal of hydroxy-protecting groups can be used in deblocking the hydroxy groups in derivatives obtained by reaction of the compounds of this invention. The deblocking may be conducted under acidic, neutral, or basic conditions as appropriate for the derivative and as appropriate for a given protecting group. Protecting groups capable of removal under acidic conditions, e.g., alkyl, tetrahydrofuranyl, tetrahydropyranyl and phenacyl can be removed in the presence of, for example, mineral acids such as hydrobromic acid or in the presence of boron tribromide. Protecting groups capable of removal under basic conditions, e.g., acyl, ethoxycarbonyl, and 2,2,2-trichloroethoxycarbonyl can be removed in the presence of, for example, aqueous alkali hydroxides such as aqueous sodium hydroxide or potassium hydroxide so as to generate hydroxy anion moieties which can be protonated by treatment with acid.

Reactions which can be undergone by the compounds of this invention include nucleophilic addition, oxidation, reduction, and condensation reactions. The reaction can be used to provide phenylhydroquinone and phenylcatechol compounds having desired physical or chemical properties, e.g., a desired solubility, diffusivity, or chemical reactivity. An exemplary application is the provision of a substituent group on the biphenyl ring structure which is appropriate to render the resultant compound substantially non-diffusible. Such a substituent group may be provided by reacting a compound of this invention with a long chain alkyl amine to form the corresponding Schiff base followed by reduction of the —C=N— bond. A non-diffusible phenylhydroquinone or phenylcatechol may also be provided by attachment of a compound of this invention to a polymer backbone, e.g., by reaction with polyvinyl alcohol to form the polymeric acetal. The products derived from the compounds of this invention can be used in various applications as redox reagents, e.g., as antioxidants or as developing agents in photographic processes.

It should be understood that reaction of the formyl group of the compounds of this invention can be used to append the biphenyl compound to a relatively large molecular fragment and that such a reaction may be considered as substitution or incorporation of the biphenyl compound onto or into the larger molecule. Alternatively, reaction of the formyl group can be used to append a relatively small molecular fragment to the biphenyl compound and such a reaction may be considered as provision of a substituent on the biphenyl compound.

Compounds of this invention wherein R is hydrogen are, of course, redox reagents and may accordingly be used in such capacity. Generally, however, such compounds will be employed as reactive intermediates, as described herein.

The following examples are provided to further illustrate the present invention. The specific limitations present in the following examples are intended as illustrative and not limitative.

EXAMPLE 1

Preparation of 4′-bromomethyl-2,5-diacetoxy-1,1′-biphenyl (a) 100 Grams of 4′-methyl-2,5-dihydroxy-1,1′-biphenyl (0.5 mole) were suspended in 220 ml. of acetic anhydride and about 5 drops of sulfuric acid were added. The resultant solution was stirred at room temperature of about 25° C. for about 16 hours. Formation of a crystalline precipitate was observed. The reaction mixture was poured into ice-water and the resultant white precipitate was separated by filtration, washed with water, and dried in a vacuum oven at 60° C. for 3 days. A yield of 140 g. of 4′-methyl-2,5-diacetoxy-1,1′-biphenyl was obtained. The product had a melting range of 94°–96° C.

(b) A mixture of 28.4 g. (0.1 mole) of 4′-methyl-2,5-diacetoxy-1,1′-biphenyl prepared in section (a) of this Example, 18.7 g. (0.105 mole) of N-bromosuccinimide, and 0.25 g. (0.001 mole) of dibenzoyl peroxide in 250 ml. of carbon tetrachloride was heated at reflux for about 6 hours. The mixture was cooled and the precipitated succinimide was removed by filtration. The filtrate solvent was removed on a rotary evaporator yielding about 42 g. of a syrupy residue. The residue was mixed with 80 ml. of low boiling petroleum ether, the mixture heated to reflux with stirring, and the petroleum ether decanted. This extraction process was repeated twice more yielding 35.5 g. of a syrupy residue. This residue was then dissolved in 180 ml. of diethylether and the solution diluted with 120 ml. of n-hexanes. Cooling of the solution in dry-ice and scratching the sides of the container induced crystallization of the product. A first crop of 17.2 g. of 4′-bromomethyl-2,5-diacetoxy-1,1′-biphenyl was obtained. The mother liquor was concentrated and crystallization induced as above to yield an additional 6.5 g. of product. The procedure was repeated once again to yield a third crop of 8.3 g. Total yield was thus 32.0 g. Nuclear magnetic resonance analysis of the combined product in deuterochloroform was consistent with the structure of 4′-bromomethyl-2,5-diacetoxy-1,1′-biphenyl. The melting range of the product was 51°–53° C.

EXAMPLE 2

Preparation of 4′-dibromomethyl-2,5-diacetoxy-1,1′-biphenyl

A mixture of 13.0 g. (0.046 mole) of 4′-methyl-2,5-diacetoxy-1,1′-biphenyl, prepared as described in Example 1(a), 18 g. (0.1 mole) of N-bromosuccinimide, and 0.5 g. of dibenzoyl peroxide (0.0005 mole) in 150 ml. of carbon tetrachloride was heated at reflux for about 15 hours. The mixture was cooled and the precipitated succinimide was removed by filtration. The filtrate was washed with cold water and dried over anhydrous sodium sulfate. The filtrate solvent was removed on a rotary evaporator yielding a solid. The solid was recrystallized from a 2:1 by volume mixture of hexane:ether, yielding about 15.6 g. of 4′-dibromomethyl-2,5-diacetoxy-1,1′-biphenyl, m.p. 95°–97° C. The product gave a single spot on TLC (Whatman K5F Silica Gel; 20% n-hexane, 80% chloroform eluent) and proton nuclear magnetic resonance and infrared spectral data confirmed the structure of the product.

EXAMPLE 3

Preparation of 4′-formyl-2,5-dihydroxy-1,1′-biphenyl

A solution of 3.63 g. (0.01 mole) of 4′-bromomethyl-2,5-diacetoxy-1,1-biphenyl, prepared as described in Example 1, and 1.04 g. (0.01 mole) of hexamethylenetetramine in 40 ml. of acetonitrile was heated at reflux under nitrogen for about 6 hours. The solution was cooled, the solvent removed on a rotary evaporator, and the resultant residue dissolved in 30 ml. of methanol. The methanol solution was diluted with 100 ml. of water and 10 ml. of concentrated hydrochloric acid and heated at reflux under nitrogen for about 1 hour. Most of the methanol was then removed on a rotary evaporator and the concentrated mixture was diluted with water and cooled to give 1.2 g. of 4′-formyl-2,5-dihydroxy-1,1′-biphenyl as an off-white solid, m.p., 202°–204° C. Thin layer chromatography indicated one component and proton nuclear magnetic resonance and infrared spectral data confirmed the structure of the product.

EXAMPLE 4

Preparation of 4′-formyl-2,5-dihydroxy-1,1′-biphenyl

A mixture of about 4.4 g. (0.01 mole) of 4′-dibromomethyl-2,5-diacetoxy-1,1′-biphenyl, prepared as described in Example 2, and about 4.4 g. (0.03 mole) of sodium acetate trihydrate in a mixture of 50 ml. of methanol and 25 ml. of water was heated at reflux under nitrogen for about 4 hours. 5 ml. of concentrated hydrochloric acid were added and refluxing continued for an additional 1½ hours. Most of the methanol was removed by evaporation on a steam bath under nitrogen resulting in precipitation of a light cream colored solid. The mixture was diluted with 50 ml. of water, cooled in an ice bath, and the resultant solid filtered, washed with water, and dried in a vacuum oven. Yield of about 2.0 g. of 4′-formyl-2,5-dihydroxy-1,1′-biphenyl, m.p. 203°–205° C. Thin layer chromatography indicated one component. Proton nuclear magnetic resonance and infrared spectra confirmed the structure and were essentially identical to the spectra obtained from the product of Example 3. The product gave a positive test with 2,4-dinitrophenylhydrazine spray reagent.

I claim:

1. A compound of the formula

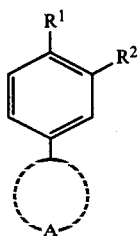

wherein one of $R^1$ and $R^2$ is hydrogen and the other is —CHO and the cyclic moiety A is -2,5-; -2,3-; or -3,4-di-OR-1-phenyl moiety wherein R is hydrogen or a hydroxy-protecting group capable of removal so as to regenerate the hydroxy group.

2. A compound of claim 1 wherein R is a hydroxy-protecting group selected from the group consisting of lower alkyl having 1 to 6 carbon atoms, methoxymethyl, methylthiomethyl, phenacyl, p-bromophenacyl, 2-tetrahydrofuranyl, 2-tetrahydropyranyl, ethoxycarbonyl, 2,2,2-trichloroethoxycarbonyl, and acyl.

3. A compound of claim 2 wherein R is acyl.
4. A compound of claim 3 wherein R is acetyl.
5. A compound of claim 1 wherein R is hydrogen.
6. A compound of claim 1 wherein $R^1$ is —CHO and $R^2$ is hydrogen.
7. A compound of claim 1 wherein said cyclic moiety A is the said 2,5-di-OR-1-phenyl moiety.
8. A compound of claim 7 wherein R is hydrogen.
9. A compound of the formula

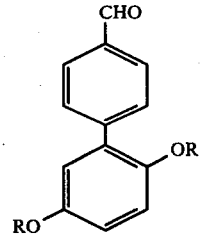

wherein R is hydrogen or a hydroxy-protecting group capable of removal so as to regenerate the hydroxy group.

10. A compound of claim 9 wherein R is a hydroxy-protecting group selected from the group consisting of lower alkyl having 1 to 6 carbon atoms, methoxymethyl, methylthiomethyl, phenacyl, p-bromophenacyl, 2-tetrahydrofuranyl, 2-tetrahydropyranyl, ethoxycarbonyl, 2,2,2-trichloroethoxycarbonyl, and acyl.

11. A compound of claim 10 wherein R is acyl.
12. A compound of claim 11 wherein R is acetyl.
13. A compound of claim 9 wherein R is hydrogen.

* * * * *